United States Patent [19]

Gagnebien-Cabanne

[11] Patent Number: 5,547,678
[45] Date of Patent: Aug. 20, 1996

[54] COMPOSITIONS AND METHODS FOR COMBATING BLEMISHES AND/OR AGEING OF THE SKIN

[75] Inventor: Francoise Gagnebien-Cabanne, Chatillon, France

[73] Assignee: L'Oreal, Paris, France

[21] Appl. No.: 399,545

[22] Filed: Mar. 7, 1995

[30] Foreign Application Priority Data

Mar. 8, 1994 [FR] France .................................. 94 02656

[51] Int. Cl.$^6$ ...................................................... A61K 7/40
[52] U.S. Cl. .............................. 424/401; 424/59; 424/60; 424/78.03; 514/846; 514/859
[58] Field of Search ................................ 424/78.03, 401, 424/59, 60; 514/846, 859

[56] References Cited

U.S. PATENT DOCUMENTS

| | | | |
|---|---|---|---|
| 5,004,594 | 4/1991 | Richard et al. | 424/47 |
| 5,362,494 | 11/1994 | Zysman et al. | 424/401 |
| 5,443,840 | 8/1995 | Morancais et al. | 424/450 |

FOREIGN PATENT DOCUMENTS

| | | |
|---|---|---|
| 381057 | 8/1990 | European Pat. Off. . |
| 531192 | 3/1993 | European Pat. Off. . |

Primary Examiner—Thurman K. Page
Assistant Examiner—Sharon Howard
Attorney, Agent, or Firm—Oblon, Spivak, McClelland, Maier, & Neustadt, P.C.

[57] ABSTRACT

Compositions containing, in a cosmetically and/or dermatologically acceptable medium, kojic acid and an ultraviolet screening agent chosen from the group consisting of benzylidenecamphor and derivatives thereof are effective for combating and/or preventing skin blemishes and for combating and/or preventing the ageing of skin.

16 Claims, No Drawings

COMPOSITIONS AND METHODS FOR COMBATING BLEMISHES AND/OR AGEING OF THE SKIN

BACKGROUND OF THE INVENTION

1. Field of the Invention

The present invention relates to cosmetic and/or dermatological compositions useful for preventing and/or combating skin blemishes and/or for combating the ageing of the skin. The present composition may be provided in the form of a smooth white cream which may be applied to the human face, body and/or legs and more especially to the hands. The present invention also relates to the dermatological treatment of the skin and to a method of combating skin blemishes and the ageing of the skin by applying such a composition to the skin.

2. Discussion of the Background

During the ageing process, various signs which are very characteristic of this ageing appear on the skin, reflected especially in a modification of the cutaneous structure and functions. This ageing is physiological in nature but may also be photo-induced, that is to say due to a repeated exposure of the skin to sunlight, especially ultraviolet light. The action of this light on the constituents of the skin and on the sebum secreted by the skin results, in particular, in the formation of oxygenated free radicals. These radicals cause considerable damage, especially in cell membranes (permeability of the membranes), in cell nuclei (mutation by action on RNA or DNA) and on tissues (necrosis and degeneration); it is thus necessary to protect the skin from these free radicals.

The main clinical signs of cutaneous ageing are especially the appearance of deep wrinkles and fine lines, which increase with age. In particular, disruption of the "grain" of the skin is observed, that is to say that the microrelief is less uniform and is anisotropic in nature.

Moreover, the skin complexion is generally modified; it appears paler and yellower, which seems to be due essentially to disruption of the microcirculation (less haemoglobin in the dermal capillaries). Furthermore, many colored and/or darker blemishes appear on the skin surface, and more especially on the hands, imparting heterogeneity to the skin. In general, these blemishes are due to considerable production of melanin in the skin epidermis and/or dermis. In some cases, these blemishes may become cancerous. Thus, it is increasingly sought to reduce these blemishes, or even to eliminate them. Moreover, diffuse irritations, and sometimes telangiectasia, may occur in certain areas of the skin.

Another clinical sign of ageing is the dry and rough appearance of the skin, which is essentially due to a more considerable desquamation; by diffracting light rays, these squama also contribute towards the somewhat grey appearance of the complexion.

Finally, a loss of firmness and of tonicity of the skin are observed which, as in the case of wrinkles and fine lines, is at least partly explained by a dermal and epidermal atrophy and flattening out of the dermoepidermal formation; the skin is thinner and more flaccid, and the thickness of the epidermis decreases.

It is thus observed that the clinical signs of cutaneous ageing result essentially from a dysfunction of the main biological mechanisms occurring in the skin.

It is known, from document JO2-200,622, to combine kojic acid with a compound chosen from derivatives of para-aminobenzoic acid, salicylic acid or methoxycinnamic acid and benzophenone derivatives in order to prevent the skin pigmentation and erythema induced by ultraviolet rays.

Moreover, a bleaching composition containing a flavonoid, kojic acid, butylmethoxydibenzoylmethane and methoxycinnamate, which act as ultraviolet screening agents, is known from document FR-A-2,680,466. Butylmethoxydibenzoylmethane has the drawback of being photo-labile (that is to say of being destabilized in the presence of light, which is particularly inconvenient for a screening agent). Thus, in order to enhance its stability, it is necessary to combine it with another screening agent of cinnamate type, thereby complicating the manufacture of the composition.

In addition, many compositions intended to combat the signs of ageing exist on the market. Unfortunately, the effectiveness of these known compositions is often still insufficient.

Thus, there remains a need for compositions which are more effective than those of the state of the art for preventing and/or combating the ageing of the skin and/or skin blemishes.

SUMMARY OF THE INVENTION

Accordingly, it is one object of the present invention to provide novel compositions useful for combating and/or preventing skin blemishes.

It is another object of the present invention to provide novel compositions useful for combating and/or preventing the ageing of skin.

It is another object of the present invention to provide novel compositions useful for combating and/or preventing photo-induced skin blemishes and/or photo-induced ageing of the skin.

It is another object of the present invention to provide novel methods for combating and/or preventing skin blemishes.

It is another object of the present invention to provide novel methods for combating and/or preventing the ageing of skin.

It is another object of the present invention to provide novel methods for combating and/or preventing photo-induced skin blemishes and/or photo-induced ageing of the skin.

These and other objects, which will become apparent during the following detailed description, have been achieved by the inventor's discovery that compositions which contain, in a cosmetically and/or dermatologically acceptable medium, kojic acid and an ultraviolet screening agent chosen from the group consisting of benzylidenecamphor and derivatives thereof are effective for combating and/or preventing skin blemishes and the ageing of skin.

Thus, the compositions according to the present invention are capable of preventing and/or combating the onset of ageing and the existing signs of ageing, such as wrinkles and fine lines, of preventing and/or combating skin pigmentation blemishes, regardless of their origin, and of protecting the skin especially by suppression of the formation of oxygenated free radicals.

Thus, the inventor has discovered, surprisingly, that the simultaneous use of kojic acid and benzylidenecamphor and/or one of its derivatives makes it possible to attenuate wrinkles and fine lines, to modify the complexion of the skin to appear rosier, to eliminate pigmentation blemishes, to remove the squama and to give a more elastic consistency to the skin.

In particular, the composition of the present invention makes it possible to attenuate or fade out the blemishes for 50% of women who have applied this composition to the hands. This is, in fact, an unexpected curative effect which has never been achieved with the products containing kojic acid or any other depigmenting active agent which are currently available on the market.

Given the relatively low efficacy of kojic acid, it is entirely surprising that benzylidenecamphor and/or the derivatives thereof increase its antiblemish efficacy so considerably.

DETAILED DESCRIPTION OF THE PREFERRED EMBODIMENTS

The benzylidenecamphor derivatives which may be used in the invention are, in particular, the sulpho and/or sulphonato derivatives. In particular, the benzylidenecamphor derivatives which may be used in the invention have the following general formula (a):

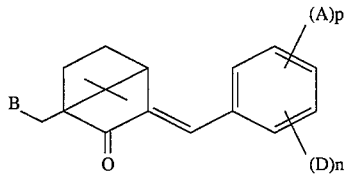

in which:
- B represents —H or —$SO_3H$, $0 \leq p \leq 1$, with B=—$SO_3H$ when p=0, $0 \leq n \leq 4$,
- D represents a linear or branched alkyl or alkoxy radical, which may be identical or different when $n \geq 2$, containing from about 1 to about 18 carbon atoms, a halo radical or a hydroxyl radical,
- A, in the meta or para position, represents: an —$SO_3H$ radical; or a group

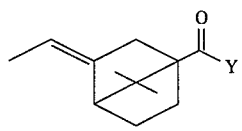

in which Y represents H or $SO_3H$; or a group

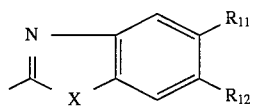

in which:
- $R_{11}$ denotes a hydrogen atom, a linear or branched alkyl or alkoxy radical containing from about 1 to about 6 carbon atoms or the —$SO_3H$ radical, $R_{11}$ being —$SO_3H$ when B=—H,
- $R_{12}$ denotes a hydrogen atom or a linear or branched alkyl or alkoxy radical containing from about 1 to about 6 carbon atoms,
- X is an oxygen or sulphur atom or a group —NR—, R being a hydrogen atom or a linear or branched alkyl radical containing from about 1 to about 6 carbon atoms, and in which at least one —$SO_3H$ function is optionally neutralized.

The neutralization of one or more functions may be achieved using a base generally used in the cosmetics field, such as sodium hydroxide, triethanolamine or potassium hydroxide. Accordingly, these compounds include sodium salts, triethanolammonium salts, and potassium salts.

Specific examples of compounds of formula (a) which may be mentioned are the derivatives of formulae (I), (II) and (III) below:

Formula (I):

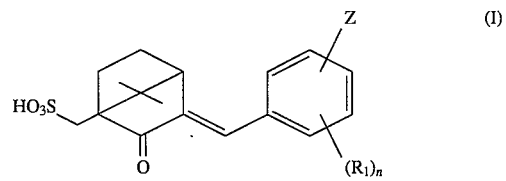

in which:
Z, preferably in the para or meta position, denotes a group

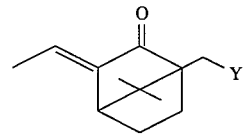

in which Y represents —H or —$SO_3H$, which is optionally neutralized,
n is equal to 0 or is a number ranging from 1 to 4 ($0 \leq n \leq 4$),
$R_1$ represents one or more linear or branched alkyl or alkoxy radicals, which may be identical or different, containing from about 1 to about 4 carbon atoms.

A particularly preferred compound of formula (I) is that corresponding to n=0, Z in the para position and Y=—$SO_3H$: benzene-1,4-[di(3-methylidene-10-camphorsulphonic)] acid which is also referred to (according to the CTFA nomenclature—5th Edition) as terephthalylidenedicamphorsulphonic acid.

Formula (II):

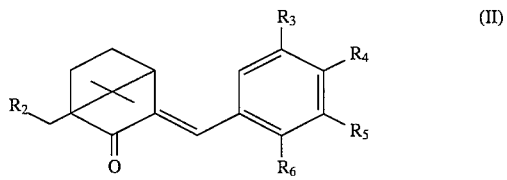

in which:
$R_2$ denotes a hydrogen atom or an —$SO_3H$ radical,
$R_3$, $R_4$, $R_5$ and $R_6$, which may be identical or different, represent a hydroxyl group, a linear or branched alkyl radical having from about 1 to about 4 carbon atoms, a linear or branched alkenyl radical having from about 2 to about 4 carbon atoms, a linear or branched alkoxy radical having from 1 to 4 carbon atoms, a linear or branched alkenyloxy radical having from 2 to 4 carbon atoms, or a halo radical; furthermore, only one radical $R_3$ to $R_6$ may be an —$SO_3H$ radical, and at least one of the radicals $R_3$ to $R_6$ denoting the —$SO_3H$ radical when $R_2$ is a hydrogen atom. One or more —$SO_3H$ functions may also be neutralized.

Specific examples which may be mentioned are the following compounds of formula (II) in which:
$R_4$ denotes the —$SO_3H$ radical in the para position of benzylidenecamphor and $R_2$, $R_3$, $R_5$ and $R_6$ each denote a hydrogen atom, that is to say 3-benzylidenecamphor-4'-sulphonic acid.

$R_3$, $R_4$, $R_5$ and $R_6$ each denote a hydrogen atom and $R_2$ denotes an —$SO_3H$ radical, that is to say 3-benzylidene-10-camphorsulphonic acid.

$R_4$ denotes a methyl radical in the para position of benzylidenecamphor, $R_5$ denotes an —$SO_3H$ radical and $R_2$, $R_3$ and $R_6$ represent a hydrogen atom, that is to say 3-benzylidenecamphor-4'-methyl-3'-sulphonic acid.

$R_4$ denotes a chlorine atom in the para position of benzylidenecamphor, $R_5$ denotes an —$SO_3H$ radical and $R_2$, $R_3$ and $R_6$ represent a hydrogen atom, that is to say 3-benzylidenecamphor-4'-chloro-3'-sulphonic acid.

$R_4$ denotes a methyl radical in the para position of benzylidenecamphor, $R_3$, $R_5$ and $R_6$ denote a hydrogen atom and $R_2$ denotes an —$SO_3H$ radical, that is to say 4'-methyl-3-benzylidene-10-camphorsulphonic acid.

$R_2$ represents an —$SO_3H$ radical, $R_3$ is a methyl radical, $R_4$ is a hydrogen atom, $R_5$ is a tert-butyl radical and $R_6$ is a hydroxyl radical, that is to say 3-(3-t-butyl-2-hydroxy-5-methyl)benzylidene-10-camphorsulphonic acid.

$R_2$ represents an —$SO_3H$ radical, $R_3$ is a methoxy radical, $R_4$ is a hydrogen atom, $R_5$ is a tert-butyl radical and $R_6$ is a hydroxyl radical, that is to say 3-(3-t-butyl-2-hydroxy-5-methoxy)benzylidene-10-camphorsulphonic acid.

$R_2$ represents an —$SO_3H$ radical, $R_3$ and $R_5$ each denote a tert-butyl radical, $R_4$ denotes a hydroxyl radical and $R_6$ denotes a hydrogen atom, that is to say 3-(3,5-di-tert-butyl-4-hydroxy)benzylidene-10-camphorsulphonic acid.

$R_4$ represents a para-methoxy radical, $R_5$ represents —$SO_3H$ and the radicals $R_2$, $R_3$ and $R_6$ represent H, that is to say 3-benzylidenecamphor-4'-methoxy-3'-sulphonic acid.

$R_2$ denotes an —$SO_3H$ radical, $R_3$ and $R_6$ represent H and $R_4$ and $R_5$ form a methylenedioxy radical, that is to say 3-(4,5-methylenedioxy)benzylidene-10-camphorsulphonic acid.

$R_2$ represents an —$SO_3H$ radical, $R_4$ represents a methoxy radical and the radicals $R_3$, $R_5$ and $R_6$ represent H, that is to say 3-(4-methoxy)benzylidene-10-camphorsulphonic acid.

$R_2$ represents an —$SO_3H$ radical, $R_4$ and $R_5$ are both a methoxy radical and the radicals $R_3$ and $R_6$ represent H, that is to say 3-(4,5-dimethoxy)benzylidene-10-camphorsulphonic acid.

$R_2$ represents an —$SO_3H$ radical, $R_4$ is an n-butoxy radical and the radicals $R_3$, $R_5$ and $R_6$ represent a hydrogen atom, that is to say 3-(4-n-butoxy)benzylidene-10-camphorsulphonic acid.

$R_2$ represents an —$SO_3H$ radical, $R_4$ is an n-butoxy radical, $R_5$ is a methoxy radical and $R_3$ and $R_6$ both denote a hydrogen atom, that is to say 3-(4-n-butoxy-5-methoxy)benzylidene-10-camphorsulphonic acid.

Formula (III):

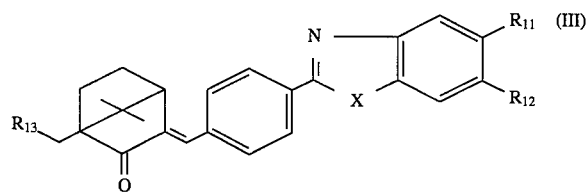

in which:

$R_{11}$ denotes a hydrogen atom, a linear or branched alkyl or alkoxy radical containing from about 1 to about 6 carbon atoms or an —$SO_3H$ radical, $R_{12}$ denotes a hydrogen atom or a linear or branched alkyl or alkoxy radical containing from about 1 to about 6 carbon atoms, $R_{13}$ denotes a hydrogen atom or an —$SO_3H$ radical, at least one of the radicals $R_{11}$ and $R_{13}$ denoting an —$SO_3H$ radical, X is an oxygen or sulphur atom or a group —NR—, R being a hydrogen atom or a linear or branched alkyl radical containing from about 1 to about 6 carbon atoms.

A specific example of a compound of formula (III) which may be mentioned is: the compound in which X denotes an —NH— radical, $R_{11}$ denotes an $SO_3H$ radical, and $R_{12}$ and $R_{13}$ both denote a hydrogen atom, that is to say 2-[4-(camphormethylidene)phenyl]benzimidazole-5-sulphonic acid.

The compounds of structures (I), (II) and (III) are described in U.S. Pat. No. 4,585,597 and in Patents FR 2,236,515, 2,282,426, 2,645,148, 2,430,938 and 2,592,380.

As other examples of benzylidenecamphor derivatives which may be used in the present invention, there may be mentioned the compounds of general formula (b) below:

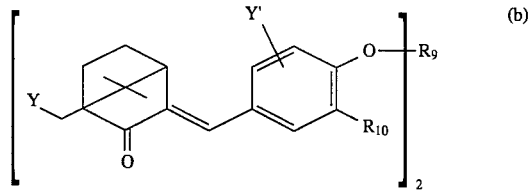

in which:

$R_9$ denotes a divalent radical: —$(CH_2)_m$— or —$CH_2$—CHOH—$CH_2$—, m being an integer ranging from 1 to 10 ($1 \leq m \leq 10$), $R_{10}$ denotes a hydrogen atom, an alkoxy radical containing from 1 to 4 carbon atoms approximately or a divalent radical —O— attached to the radical $R_9$ when the latter is also divalent, Y and Y' denote a hydrogen atom or an —$SO_3H$ radical, at least one of these radicals Y or Y' being other than hydrogen. In this case also, the —$SO_3H$ function may be neutralized.

Specific examples which may be mentioned are the following compounds of formula (b) in which Y represents —$SO_3H$, Y' is —H, $R_{10}$ is H and $R_9$ is —$CH_2$—$CH_2$—, that is to say ethylenebis[3-(4'oxybenzylidene)-10-camphorsulphonic] acid.

According to the present invention, the amount of kojic acid is that conventionally used in the cosmetics or dermatological field. As an example, it is possible to use from 0.05% to 10% by weight, based on the total weight of the composition, preferably from 0.5% to 2% by weight, based on the total weight of the composition, of kojic acid.

Similarly, the amount of benzylidenecamphor derivative which may be used in the present invention is that generally used in the fields concerned. In practice, from 0.1% to 10% by weight, based on the total weight of the composition, preferably from 0.1% to 5% by weight, based on the total weight of the composition, of the benzylidenecamphor derivative is used.

The composition of the present invention may take any pharmaceutical form normally used for a topical application, such as solutions, aqueous or aqueous-alcoholic gels, oil-in-water or water-in-oil emulsions, and more particularly droplets of oil dispersed by means of spherules in an aqueous phase. These spherules may be polymeric nanoparticles such as nanospheres and nanocapsules or, better, may be lipid vesicles. The composition of the present invention may be provided in the form of a cream, an ointment, a lotion or a serum.

The oils which may be used in the present invention are those generally used in the fields concerned. They may be plant, mineral or synthetic oils, and may optionally be silicone-containing and/or fluorinated oils.

The invention may also contain hydrophilic or lipophilic adjuvants such as gelling agents, preserving agents, opacifying agents, emulsifying agents, coemulsifying agents, neutralizing agents, fragrances and dissolving agents thereof or peptizing agents, dyes, pigments and fillers, as well as lipophilic or hydrophilic active agents other than kojic acid, benzylidenecamphor and one of the derivatives thereof.

The amounts of oil and of water are generally those used in the fields considered and depend on the pharmaceutical form of the composition. For an oil-in-water emulsion or a dispersion of oil in water by means of lipid spherules, the oil may be present in an amount of from 2% to 40% by weight, based on the total weight of the composition.

Similarly, the adjuvants are used in the usual amount and may be present in a total amount of from 0.1% to 20% by weight, based on the total weight of the composition. The amount of adjuvants depends on their nature.

Although the composition of the present invention may be applied topically to all parts of the body and of the face, it is particularly advantageous for treating the hands. Thus, the invention further relates to a method for the cosmetic treatment of the hands by applying the present composition to the hands.

Another embodiment of the present invention is a method for the cosmetic treatment of wrinkles and/or fine lines of the skin as well as a method for toning, moisturizing and/or firming the skin by applying the present composition to the skin.

A further embodiment of the present invention is a method for the cosmetic treatment of skin blemishes due to ageing, these blemishes being on the face and/or the body, including the hands and the scalp, by applying the present composition to the skin.

In the present methods, the present composition is applied to the skin in an amount sufficient to result in the kojic acid being applied to the skin in an amount of 0.001 to 0.2 mg/cm$^2$, preferably 0.01 to 0.04 mg/cm$^2$ of skin, and the benzylidenecamphor or derivative thereof being applied to the skin in an amount of 0.002 to 0.2 mg/cm$^2$ of skin, preferably 0.002 to 0.1 mg/cm$^2$ of skin. The composition may be applied one or more times daily or less frequently. In a preferred embodiment, the present composition is applied to the skin within a few hours before exposure of the skin to intense sunlight, such as sunbathing.

Other features of the invention will become apparent in the course of the following descriptions of exemplary embodiments which are given for illustration of the invention and are not intended to be limiting thereof.

EXAMPLES

The tests which follow demonstrated the advantages of the present invention. The aim of the tests was to show the ability of the compositions of the invention to counter pigmentation and the formation of erythema in skin subjected to UV.

The tests were performed on 9 subjects with 3 compositions, the first according to the present invention containing the combination of kojic acid and terephthalylidenedicamphorsulphonic acid, the second illustrating the state of the art, containing the combination of kojic acid and oxybenzophenone, and a third containing the medium free of kojic acid and of screening agents (placebo). The subjects applied the compositions twice a day morning and evening for 24 days and, on the days of irradiation, they received an additional application 2 h before the irradiation.

The irradiation was performed using an Osram 2500 W xenon lamp fitted with a WG 320 Schott filter 1 mm in thickness which cuts out a very large part of the UVB rays, as well as a water filter which cuts out the IR rays. This system reproduces a UVA-enriched solar spectrum.

The irradiation was performed over 9 days. The MED (minimum erythematous dose) of the subjects was first determined (according to the FDA recommendation 25.04.1978); on the second day, the irradiation was 0.75 MED, on the third day this was 1 MED; on the fourth and fifth days there was no irradiation; on the sixth day, the irradiation was 1.25 MED; the irradiation was then 1.5 MED for three consecutive days. There was no irradiation after the ninth day, but application of the compositions was continued and readings were taken up to the 24th day.

The percentage inhibition of erythema by means of the first and second compositions in comparison with the placebo was determined, on the one hand, via a visual evaluation conventionally used for the determination of the SPFs (sun protection factor), and the percentage inhibition of pigmentation by means of these first and second compositions in comparison with the placebo was determined, on the other hand, via measurement of the darkening of the skin using a Minolta Lab. chromameter. The percentages of inhibition are calculated relative to the placebo according to the following formulae and are shown in Table I:

$$\frac{\text{Inhibition by composition (1) or (2)} - \text{inhibition by the placebo}}{\text{Inhibition by the placebo}} \times 100$$

TABLE I

| Combinations | Inhibition of the erythema | | Inhibition of pigmentation | |
|---|---|---|---|---|
| | D3 | D9 | D9 | D24 |
| Kojic acid + terephthalylidenecamphorsulphonic acid | +54% | +78% | +48% | +82% |
| Kojic acid + oxybenzophenone | +36% | +59% | +35% | +62% |

These tests show that terephthalylidenedicamphorsulphonic acid has a markedly greater potentiating action on the effect of kojic acid than does oxybenzophenone; the inhibition of erythema and of pigmentation with the composition of the present invention are far superior (20% higher) than those obtained with the composition of the prior art.

In the examples below of cosmetic and/or dermatological compositions in accordance with the present invention, the compositions are given as a % by weight, based on the total weight of the composition.

Example 1: Anti-blemish oil-in-water cream

| | Composition | |
|---|---|---|
| $A_1$ | - Sorbitan tristearate (emulsifying agent) | 0.7% |
| | - Polyethylene glycol stearate (40 EO) (emulsifying agent) | 1.6% |
| | - Cetyl alcohol (co-emulsifying agent) | 3.2% |
| | - Glyceryl mono,di,tripalmitostearate (emulsifying agent) | 2.4% |
| | - Myristyl myristate (oil) | 2% |
| | - Liquid fraction of karite butter (oil) | 2% |
| | - Propyl para-hydroxybenzoate (preserving agent) | 0.2% |
| $A_2$ | - Cyclopentadimethylsiloxane (oil) | 15% |
| B | - Demineralized water | qs 100% |
| | - Glycerol (moisturizing agent) | 3% |
| | - Kojic acid | 1% |
| | - Methyl para-hydroxybenzoate (preserving agent) | 0.2% |
| C | - Terephthalylidenedicamphorsulphonic acid at a concentration of 33% in water | 2% |
| | - Triethanolamine (neutralizing agent) | 0.3% |
| D | - Fragrance | 0.3% |

Preparation of the phase $A_1+A_2$

The constituents of $A_1$ are dissolved at 80° C. When the mixture is clear, the temperature is lowered to 65° C., and $A_2$ is added. The mixture must be clear and homogeneous. The temperature is maintained at 65° C.

Manufacture

The constituents of B are dissolved at 85° C.–90° C. in a manufacturing beaker. After checking the clarity, the temperature is brought to 65° C. The emulsion is produced, with stirring, by pouring ($A_1+A_2$) into B. The cooling is continued with stirring. At 40° C., phase C is added, and stirring is then continued. Finally, the fragrance is added, and the mixture is allowed to cool to 20° C. with stirring.

Example 2: Oil-in-water cream

| | Composition | |
|---|---|---|
| $A_1$ | - Demineralized water | 10% |
| | - Cholesterol} | 1.5% |
| | - Polyethylene glycol monostearate}(vesicles) | 1.5% |
| | - Monosodium salt of n-stearic acid} of a-Glutamic acid | 0.2% |
| $A_2$ | - Demineralized water | 13% |
| | - Glycerine (moisturizing agent) | 3% |
| | - Phenoxyethanol (preserving agent) | 0.7% |
| B | - Apricot almond oil | 9% |
| | - Purified soya oil | 4% |
| | - Cyclopentadimethylsiloxane (oil) | 10% |
| | - Propyl para-hydroxybenzoate | 0.1% |
| | - Fragrance | 0.3% |
| C | - Carboxyvinyl polymer synthesized in methylene chloride (gelling agent) | 0.7% |
| | - Demineralized water | 36.45% |
| | - Triethanolazine (neutralizing agent) | 0.7% |
| D | - Demineralized water | 5% |
| | - Kojic acid | 1% |
| E | - Terephthalylidenedicamphorsulphonic acid at a concentration of 33% in water | 2.3% |
| | - Triethanolamine | 0.6% |

Manufacture

The constituents of $A_1$ are melted at 100° C. The melt is left to swell with stirring for 1 hour and 30 minutes. When the mixture is homogeneous, $A_2$ is added; the temperature is stabilized at 80° C. The mixture is then twice put through a high-pressure homogenizer in order to form the vesicles.

B is prepared at 70° C.; the mixture should be clear. It is cooled to 50° C. B is added to A at 50° C.

This is then twice put through the high-pressure homogenizer in order to disperse the fatty phase B. The mixture is cooled to 30° C. C is added (the gel will have been prepared beforehand in water at 80° C., by sprinkling the carboxyvinyl polymer; after the latter has swollen, the mixture is neutralized using triethanolamine with stirring; the gel should be quite smooth). D is added, followed by E. Stirring is continued for 5 minutes. The manufacture is complete.

Example 3: Gel

| | Composition | |
|---|---|---|
| A | - Demineralized water | 32% |
| | - Carboxyvinyl polymer | 0.45% |
| | - Triethanolamine | 0.45% |
| B | - Demineralized water | 59.8% |
| | - Glycerine | 3% |
| | - Methyl para-hydroxybenzoate | 0.2% |
| | - Kojic acid | 1% |
| | - Xanthan gum (gelling agent) | 0.2% |
| C | - Terephthalylidenedicamphorsulphonic acid at a concentration of 33% in water | 2.3% |
| | - Triethanolamine | 0.6% |

Manufacture

The gel (carboxyvinyl polymer) is prepared in water at 80° C., as in Example 2. After the constituents of B have been dissolved at 80° C., B is added to A. The mixture is made smooth and is left to cool with slow paddle-stirring. At 35° C., C is added. The mixture is allowed to cool to 25° C. Manufacture of the gel is complete.

Example 4: Lotion

| | Composition | |
|---|---|---|
| A | - Oxyethylenated hydrogenated ricinoleic triglycerides (60 EO) (peptizing agent) | 0.09% |
| | - Fragrance | 0.03% |
| B | - Demineralized water | qs 100% |
| | - Glycerine | 5.5% |
| | - Kojic acid | 1% |
| | - Citric acid | 1% |
| | - 99% triethanolamine | 1.9% |
| | - Imidazolidinylurea (preserving agent) | 0.3% |
| C | - Terephthalylidenedicamphorsulphonic acid at a concentration of 33% in water | 2.3% |
| | - Triethanolamine | 0.6% |

Manufacture

The constituents of A are mixed together at 40° C. When they are entirely dissolved, the constituents of B are added successively at room temperature. Stirring is continued, and full dissolution of the constituents is verified. C is added; the mixture should be clear. The manufacture is complete.

This application is based on French Patent Application No. 94-02656, filed on Mar. 3, 1994, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A composition for preventing and/or combating skin blemishes and/or for combating ageing of the skin, comprising, in a cosmetically and/or dermatologically acceptable medium, (a) kojic acid and (b) an ultraviolet screening agent selected from the group consisting of benzylidenecamphor and functional derivatives thereof.

2. The composition of claim 1, wherein said ultraviolet screening agent is a sulpho or sulphonato functional derivative of benzylidenecamphor.

3. The composition of claim 1, wherein said benzylidenecamphor derivative has the formula (I):

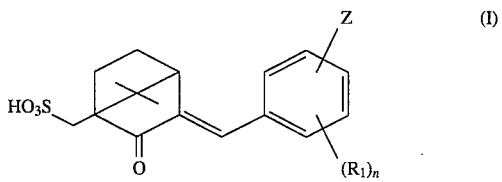

wherein:

Z denotes a group

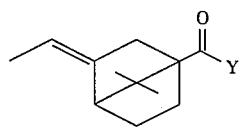

in which Y represents —H or —SO₃H, which is optionally neutralized, n is equal to 0 or is a number ranging from 1 to 4 ($0 \leq n \leq 4$), $R_1$ represents one or more linear or branched alkyl or alkoxy radicals, which may be identical or different, having from 1 to 4 carbon atoms.

4. The composition of claim 1, wherein said benzylidenecamphor derivative is benzene-1,4-[di(3-methylidene-10-camphorsulphonic)] acid.

5. The composition of claim 1, which is in the form of an oil-in-water emulsion or in the form of a dispersion of spherules.

6. The composition of claim 5, wherein said spherules are lipid spherules.

7. The composition of claim 1, wherein said kojic acid is present in an amount of from 0.05% to 10% by weight, based on the total weight of said composition.

8. The composition of claim 1, wherein said ultraviolet screening agent is present in an amount of from 0.1% to 10% by weight, based on the total weight of said composition.

9. The composition of claim 1, further comprising a hydrophilic or lipophilic adjuvant.

10. The composition of claim 9, said hydrophilic or lipophilic adjuvant is selected from the group consisting of gelling agents, preserving agents, fragrances, fillers, dyes, and active agents other than kojic acid and said ultraviolet screening agent.

11. A method of treating skin blemishes due to ageing, comprising applying to the skin of a subject in need thereof an effective flemish treating amount of a composition, comprising in a cosmetically and/or dermatologically acceptable medium, (a) kojic acid and (b) an ultraviolet screening agent selected from the group consisting of benzylidenecamphor and derivatives thereof.

12. The method of claim 11, wherein said composition is applied to said subject's hands.

13. A method of treating wrinkles and/or fine lines on the skin, comprising applying to the skin of a subject in need thereof an effective wrinkle and/or fine line treating amount of a composition comprising in a cosmetically and/or dermatologically acceptable medium, (a) kojic acid and (b) an ultraviolet screening agent selected from the group consisting of benzylidenecamphor and derivatives thereof.

14. The method of claim 13, wherein said composition is applied to said subject's hands.

15. A method of toning, moisturizing and/or firming the skin, comprising applying to the skin of a subject in need thereof an effective taning, moisturizing and/or firming amount of a composition comprising in a cosmetically and/or dermatologically acceptable medium, (a) kojic acid and (b) an ultraviolet screening agent selected from the group consisting of benzylidenecamphor and derivatives thereof.

16. The method of claim 15, wherein said composition is applied to said subject's hands.

* * * * *